US010022195B2

United States Patent
Scholan

(10) Patent No.: US 10,022,195 B2
(45) Date of Patent: Jul. 17, 2018

(54) USER INTERFACE FOR A ROBOT

(71) Applicant: CMR Surgical Limited, Cambridge (GB)

(72) Inventor: Andrew Scholan, Newmarket (GB)

(73) Assignee: CMR Surgical Limited, Cambridge (GB)

( * ) Notice: Subject to any disclaimer, the term of this patent is extended or adjusted under 35 U.S.C. 154(b) by 87 days.

(21) Appl. No.: 15/075,910

(22) Filed: Mar. 21, 2016

(65) Prior Publication Data

US 2016/0270867 A1    Sep. 22, 2016

(30) Foreign Application Priority Data

Mar. 20, 2015  (GB) .................................. 1504787.1

(51) Int. Cl.
*A61B 34/37* (2016.01)
*A61B 34/30* (2016.01)
(Continued)

(52) U.S. Cl.
CPC .............. *A61B 34/30* (2016.02); *A61B 34/25* (2016.02); *A61B 34/37* (2016.02); *A61B 34/70* (2016.02);
(Continued)

(58) Field of Classification Search
CPC ......... A61B 34/25; A61B 34/30; A61B 34/37; A61B 34/70; A61B 34/74; A61B 90/361;
(Continued)

(56) References Cited

U.S. PATENT DOCUMENTS

| | | | |
|---|---|---|---|
| 5,631,973 A | * | 5/1997 | Green ........................ B25J 3/04 382/128 |
| 5,762,458 A | * | 6/1998 | Wang ..................... A61B 17/11 414/1 |

(Continued)

FOREIGN PATENT DOCUMENTS

| | | |
|---|---|---|
| WO | WO 00/030548 | 6/2000 |
| WO | WO 00/30548 | 6/2000 |

OTHER PUBLICATIONS

EP Application No. GB1604721.9, Search Report dated Aug. 23, 2016.

(Continued)

*Primary Examiner* — Leslie A Nicholson, III
(74) *Attorney, Agent, or Firm* — Kilpatrick Townsend & Stockton LLP

(57) ABSTRACT

A robotic system including: a robot arm; a camera for capturing motion of the robot arm; an input mechanism for detecting user input; a display device; and a controller. The controller can operate in (i) a first mode configured to drive the display device to display a video stream captured by the camera in a first format and to drive the robot arm such that motion by the user in a first direction causes the robot arm to move a reference part in a second direction; and (ii) a second mode configured to drive the display device to display the video stream in a second format reflected with respect to the first format and to drive the robot arm such that motion by the user in the first direction causes the robot arm to move the reference part in a direction opposite to the second direction.

19 Claims, 3 Drawing Sheets

(51) Int. Cl.
- *A61B 34/00* (2016.01)
- *B25J 3/00* (2006.01)
- *B25J 13/06* (2006.01)
- *B25J 9/16* (2006.01)
- *B25J 19/04* (2006.01)
- *B25J 3/04* (2006.01)
- *A61B 90/50* (2016.01)
- *A61B 90/00* (2016.01)
- *A61B 17/00* (2006.01)

(52) U.S. Cl.
CPC . B25J 3/00 (2013.01); B25J 3/04 (2013.01); B25J 9/16 (2013.01); B25J 13/06 (2013.01); B25J 19/04 (2013.01); *A61B 2017/00199* (2013.01); *A61B 2017/00207* (2013.01); *A61B 2090/3612* (2016.02); *A61B 2090/372* (2016.02); *A61B 2090/502* (2016.02); *B25J 9/1669* (2013.01); *B25J 9/1689* (2013.01); *G05B 2219/39122* (2013.01)

(58) Field of Classification Search
CPC ...... A61B 2090/3612; A61B 2090/372; A61B 2090/502; A61B 2090/364; A61B 2017/00199; A61B 2017/00207; G05B 2219/39122; B25J 3/00; B25J 3/04; B25J 19/04; B25J 13/06; B25J 9/16; B25J 9/1669; B25J 9/1689
USPC ....... 700/248, 250, 251, 257, 258, 259, 262, 700/264
See application file for complete search history.

(56) References Cited

U.S. PATENT DOCUMENTS

| | | | | |
|---|---|---|---|---|
| 5,808,665 | A * | 9/1998 | Green | B25J 3/04 348/65 |
| 5,876,325 | A * | 3/1999 | Mizuno | A61B 1/00048 600/102 |
| 6,459,926 | B1 * | 10/2002 | Nowlin | A61B 34/70 600/102 |
| 6,659,939 | B2 * | 12/2003 | Moll | A61B 19/2203 600/102 |
| 7,239,940 | B2 * | 7/2007 | Wang | A61B 34/70 318/568.11 |
| 7,297,142 | B2 * | 11/2007 | Brock | A61B 5/0086 348/65 |
| 7,331,967 | B2 * | 2/2008 | Lee | A61B 34/71 600/407 |
| 7,608,083 | B2 * | 10/2009 | Lee | A61B 17/0469 606/1 |
| 7,744,622 | B2 * | 6/2010 | Brock | A61B 34/71 606/205 |
| 8,526,737 | B2 * | 9/2013 | Green | B25J 3/04 348/45 |
| 8,918,207 | B2 * | 12/2014 | Prisco | B25J 9/1689 180/19.1 |
| 8,918,214 | B2 * | 12/2014 | Bosscher | B25J 5/005 700/260 |
| 9,179,979 | B2 * | 11/2015 | Jinno | A61B 34/71 |
| 9,718,190 | B2 * | 8/2017 | Larkin | B25J 9/1692 |
| 2010/0228249 | A1 | 9/2010 | Mohr et al. | |

OTHER PUBLICATIONS

Search Report issued by the UK intellectual Property Office dated Aug. 20, 2015 for GB Patent Appl. No. 1504787.1.

* cited by examiner

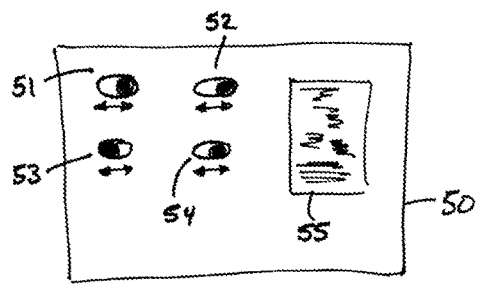
Fig. 3
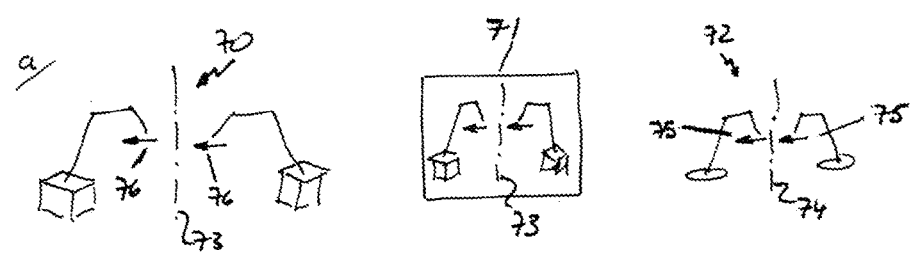
Fig. 4
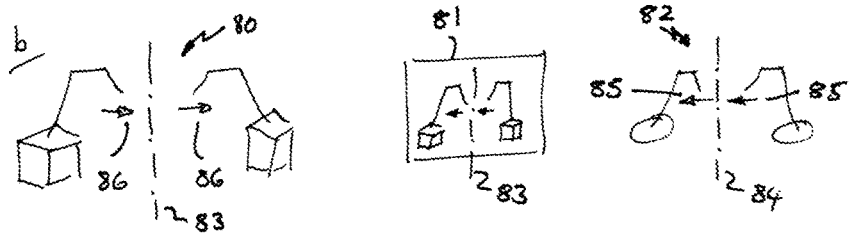
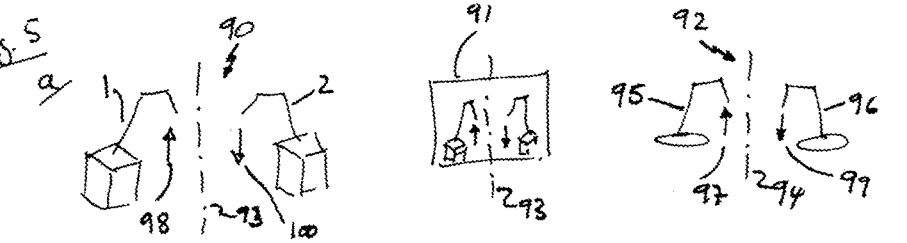
Fig. 5
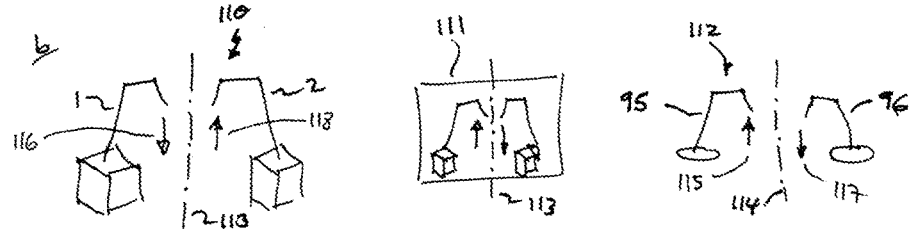

USER INTERFACE FOR A ROBOT

REFERENCE TO RELATED APPLICATION

This application claims priority to United Kingdom Patent Application No. 1504787.1, entitled "User Interface For A Robot," filed Mar. 20, 2015, the entirety of which is hereby incorporated by reference herein.

FIELD OF INVENTION

The present disclosure relates to a user interface for a robot, for example a surgical robot.

BACKGROUND

Robots are commonly used for a range of industrial tasks, and also for performing surgery. Robots can operate purely under programmatic control or they can be configured to respond to inputs in real time from a user interface. In the most complex and critical tasks, such as surgery, it is normal for a robot to operate under real-time command of an operator. To achieve this, the operator is presented with a suitable input mechanism. This is typically a physical mechanism that can be moved by the operator in three dimensions. The control system of the robot senses the configuration of the input mechanism. The control system is programmed to cause the robot arm/manipulator to move in response to the sensed configuration of the control mechanism. Additionally, it is normal for the robot to present to the user a visual indication of the state of the robot, to help the operator understand what inputs are required to achieve a certain task. The visual indication may be a video stream captured by a camera on or near the robot arm and presented to the operator on a display screen.

Some tasks that might be performed by a robot in this way require significant dexterity on the part of the user. An example of such a task is performing suturing using a surgical robot. It may be necessary to make fine and precise sutures using instruments attached to surgical robot arms, whilst the instruments are constrained within a working cavity in the body of a patient. Forming such sutures by means of a user interface of the type described above can place extreme demands on the operator's precision of movement. This can be time-consuming, extending the time for which the patient is under surgery and making the operator more tired.

One proposal for addressing this problem has been to automate tasks of this nature. For example, "Autonomous Suturing using Minimally Invasive Surgical Robots" (H Kang and J Wen, Proc. 2000 IEEE Int. Conf. on Control Applications) discusses algorithms for performing automatic robotic suturing. Approaches of this type suffer from a number of problems. First, whilst it may be feasible to automatically suture on well-characterised substrates, for example substantially planar tissue joins, it is considerably harder to automate suturing on more complex structures. In addition, a skilled surgeon may modify the size and placement of sutures depending on his knowledge of neighbouring features such as blood vessels. Second, many delicate surgical tasks are not standardised and must be adapted to an individual operation. For example, in hand surgery it may be necessary to perform a procedure on a certain part of a tendon when access to that point is hampered by bones, nerves etc. Since those obstacles vary depending on the patient, such a task is infeasible to automate.

Most people are more able to perform complex tasks with one hand than with the other. The majority of people are right-handed. When a right-handed operator is controlling a surgical robot he will typically be better able to control the robot to perform delicate tasks using his right hand. However, the nature of the surgical operation may be such that the robot arm or instrument that has to be moved in a delicate way is being controlled by the operator's left hand. In this situation some robotic user interfaces will allow the operator to lock the right-hand arm or instrument so that the user can transfer his right hand to the controller for the left-hand arm or instrument. However, in this configuration the user is no longer able to move both arms or instruments simultaneously.

There is a need for an improved way of controlling a robot.

SUMMARY

According to the present disclosure there is provided a robotic system comprising: a robot arm; a camera for capturing a video stream representing motion of the robot arm; an input mechanism for detecting the motion of a user; a display device; and a controller for driving the robot arm to operate in response to motion of the user as detected by the input mechanism and for driving the display device to display a video stream captured by the camera; the controller being capable of operating in a first mode in which it drives the display device to display the captured video stream in a first format and in which it drives the robot arm such that motion by the user in a first direction as detected by the input mechanism causes the robot arm to move a reference part in a second direction; and a second mode in which it drives the display device to display the captured video stream in a second format reflected with respect to the first format and in which it drives the robot arm such that motion by the user in the first direction as detected by the input mechanism causes the robot arm to move the reference part in a direction opposite to the second direction.

The format may be a display format. The controller may be configured to operate as aforesaid. The system may comprise a user interface input for selecting between the two modes.

The system may comprise a second robot arm. The input mechanism may be capable of independently detecting motion of two hands of the user. The controller may be configured so as to: in the first mode drive the motion of a first one of the robot arms in dependence on a motion sensed in respect of a first hand of the user, and the motion of a second one of the robot arms in dependence on a motion sensed in respect of a second hand of the user; and in the second mode drive the motion of the second one of the robot arms in dependence on a motion sensed in respect of the first hand of the user, and the motion of the second one of the robot arms in dependence on a motion sensed in respect of the first hand of the user.

The input mechanism may comprise one or more mechanical linkages, each linkage being movable by a respective hand of the user to detect motion of the user.

The input mechanism may comprise one or more detectors configured for remotely sensing the motion of the user.

The reflected format may be a format in which the image is reflected about an axis that is vertical with respect to the display device.

The reflected format may be a format in which the image is reflected about an axis that is vertical with respect to the user.

The first direction may be horizontal.

The controller may be configured such that in both the first and second modes it drives the robot arm such that motion of the user in a third direction orthogonal to the first direction as detected by the input mechanism causes motion of the reference part in a fourth direction orthogonal to the second direction.

The system may comprise a dedicated input device for selecting whether the controller operates in the first mode or the second mode.

The reference part may be or may be at the distal end of the arm. The reference part may be or may be at the distal tip of an instrument mounted on the arm.

The camera may be carried by a robot arm. The camera may be fixed with respect to a base on which the robot arm is supported.

The system may be a surgical robotic system.

According to another aspect of the present disclosure there is provided a robotic system comprising: a first robot arm; a second robot arm; a camera for capturing a video stream representing motion of the first and second robot arms; a display device; an input mechanism for detecting the motion of a user, the input mechanism being capable of independently detecting motion of two hands of the user; and a controller for driving the robot arm to operate in response to motion of the user as detected by the input mechanism, the controller being configured so as to: in a first mode drive the motion of a first one of the robot arms in dependence on a motion sensed in respect of a first hand of the user, and the motion of a second one of the robot arms in dependence on a motion sensed in respect of a second hand of the user and drive the display device to display the captured video stream in a first format; and in a second mode drive the motion of the second one of the robot arms in dependence on a motion sensed in respect of the first hand of the user, and the motion of the second one of the robot arms in dependence on a motion sensed in respect of the first hand of the user and drive the display device to display the captured video stream in a second format reflected with respect to the first format.

For the robotic systems, the controller may be configured to operate in the first mode or the second mode independently of the position of the camera. The operational mode may be independent of the orientation and/or attitude of the camera. That is, the robotic system may be arranged so that the processor switches from the first mode to the second mode, or the second mode to the first mode, independently of the position and/or orientation of the camera.

These embodiments are mentioned not to limit or define the limits of the present subject matter, but to provide examples to aid understanding thereof. Illustrative embodiments are discussed in the Detailed Description, and further description is provided there. Advantages offered by various embodiments may be further understood by examining this specification and/or by practicing one or more embodiments of the claimed subject matter.

BRIEF DESCRIPTION OF DRAWINGS

Aspects of the present disclosure will now be described by way of example with reference to the accompanying drawings.

FIG. 3 illustrates a user interface display according to some aspects of the present disclosure.

FIGS. 4 and 5 illustrate normal and inverted modes of operation according to some aspects of the present disclosure.

DETAILED DESCRIPTION

Figure 1:
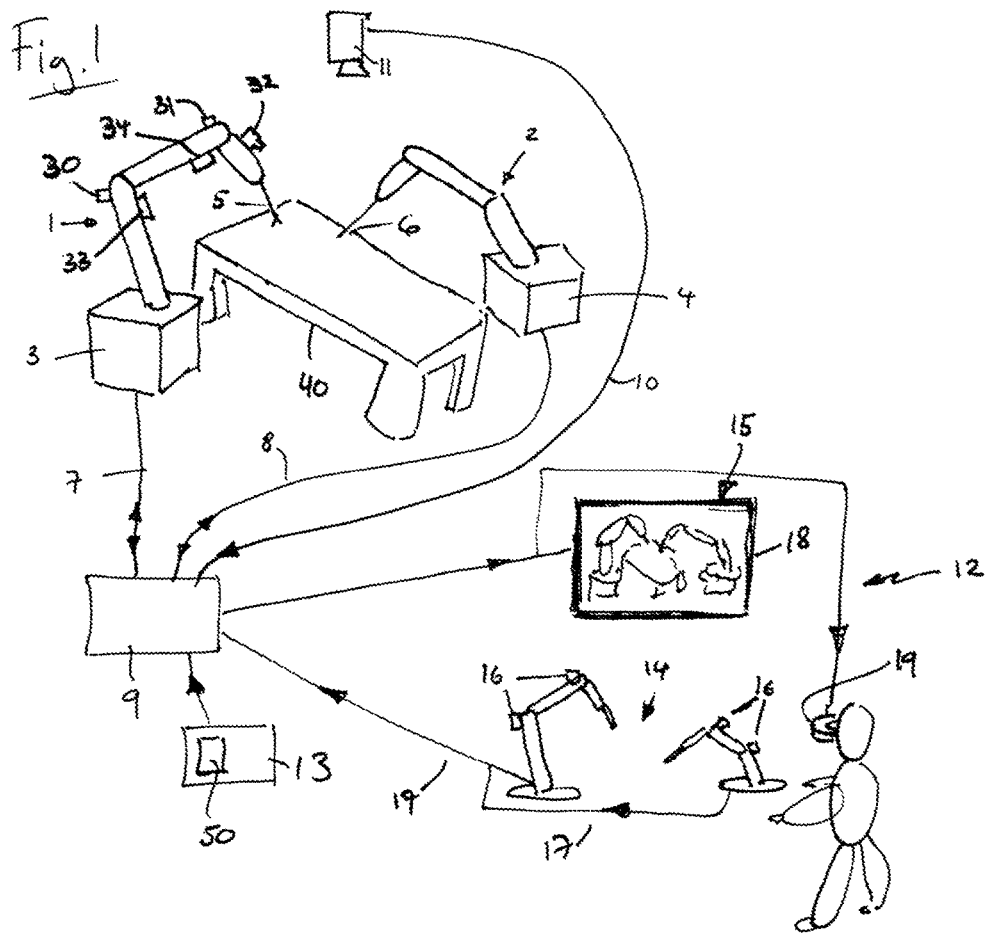
FIG. 1 is a schematic diagram of a surgical robot system according to some aspects of the present disclosure.

The robot system shown in FIG. 1 is capable of operating in two modes. The robot system has two robot arms which can be controlled by the motions of a user, whilst the user views on a display a real-time video stream representing the state of the robot arms. In one mode there is a relationship between the controls, the display and the arms such that the user perceives one robot arm as being controlled by his right hand and the other arm as being controlled by his left hand. In a second mode that relationship is reversed. In addition, the system maintains a relationship between the control dynamics and the view on the display so that whether the system is operating in the first mode or the second mode the motion of the robots appears to the user to be naturally related to the motion of his hands. As will be described further below, this involves reversing the response of the robots to control motions of the user having a left-right component when the system is in the second mode, and mirroring the output to the display when the system is in the second mode.

FIG. 1 shows a surgical robot system. The system comprises first and second robot arms 1, 2. Each arm comprises a series of rigid links joined by articulated joints, whereby the configuration of each arm can be altered when the robot is in use. Each joint may provide rotational and/or translational freedom. The proximal end of each arm is mounted to a base 3, 4. The bases are moved to the required location before a surgical procedure is performed and are then fixed in place for the duration of the procedure. The bases may stand on the floor, as illustrated in FIG. 1, or may be attached to the ceiling or wall or to an operating table. The distal end of each arm terminates in an instrument 5, 6. The instrument is a tool for performing some operational function, for example cutting, grasping, irradiating or imaging. The instrument may terminate in an end effector such as a cutter, pincer, laser or camera.

Each base 3, 4 is coupled by a data connector 7, 8 to a control unit 9. The system comprises a camera 11 coupled to the control unit 9. The control unit also receives an input at 10 from a camera 11 which has an overview of the operation of the robot arms 1, 2. That is, the camera may be positioned to have an overview of the robot arms and is operable to capture a video stream formed from a sequence of captured images. The camera may be an endoscope. It may be mounted on to an arm of the robotic system. The arm on which the camera is mounted may be a third arm separate to the arms 1, 2. The endoscope may be positioned within the cavity of a patient during a surgical procedure. The camera may be positioned to view the surgical site during a procedure and to capture a view of the distal ends of the robotic arms 1, 2. That is, the camera may be positioned to capture a view of the distal ends of the end effectors.

The controller also interfaces to a user interface shown generally at 12. The user interface comprises an operational control unit 13, arm control input devices 14 and a display 15.

The operational control unit 13 is an interface for setting the operating modes of the arm. The operational control unit may comprise a series of switches by means of which an operator may indicate to the control unit 9 the manner in which the robot is to operate. For example, the operational control unit can be used to enable or disable the arm control input devices 14. The operational control unit may comprise indicators and/or a display for providing information on the operational condition of the robot.

The arm control input devices 14 provide a user interface input function whereby an operator of the robot can indicate to the control unit desired motions of the arms 1, 2. In one example, as illustrated in FIG. 1, each arm control input device can be an articulated linkage comprising sensors 16 for sensing the configuration of each link. The operator can move the linkages in three dimensions, and the configuration of each linkage indicates the desired configuration of a respective one of the arms 1, 2. Conveniently, the articulations of the linkages may mimic the linkages of the arms and/or the instruments. The outputs of the configuration sensors are passed to the control unit 13 via lines 17. In another example the arm control input devices could be a series of wireless position sensors and an associated processing function that can together sense the position of the operator's hands, arms or other body parts. For example, the zone in which the operator works can be imaged by cameras from multiple angles and an image processor can process the outputs of the cameras to determine the locations of the operator's hands in three dimensions. Again, that information would be passed to the control unit 13.

If the camera 11 is an endoscope attached to its own arm, that arm may also be controllable by the arm control input devices 14. For example, one of the input devices 14 may comprise a joystick operable by a user to control the motion of the arm/endoscope. Conveniently, the joystick may be positioned on the input device so as to be manipulated and/or actuated by the user's thumb. That is, the input device may comprise a thumb joystick for controlling motion of the endoscope 11. This may enable the surgeon to concurrently control the motion of the arms 1, 2 and the endoscope. If there is only one endoscope, only one of the arm control input devices 14 need have an endoscope controller (e.g. in the form of thumb joystick). However, both arm control input devices may comprise an endoscope controller to control motion of the endoscope 11. This may conveniently allow a surgeon to use either their right thumb or left thumb to control the endoscope.

The display 15 may comprise one or more display screens 18, or it may be provided as a headset 19 that can be worn by the operator. The display 15 may display, or output, a video stream and/or image derived from the video stream and/or image captured by the camera 11. The video stream output by display 15 may or may not correspond directly to the video stream captured by the camera 11. In a first set of operational modes the video stream output by the display is (that is, directly corresponds to) the video stream captured by the camera. In other operational modes, the video stream output by the display 15 is derived from, but is not the same as, the video stream captured by the camera 11. In some examples, the camera 11 may be fixed in space (i.e. have a fixed position and orientation) as the robotic system transitions from one operational mode to another. More generally, the operational mode of the robotic system may be controlled independently of the position of the endoscope. This will be explained in more detail below.

Figure 2:
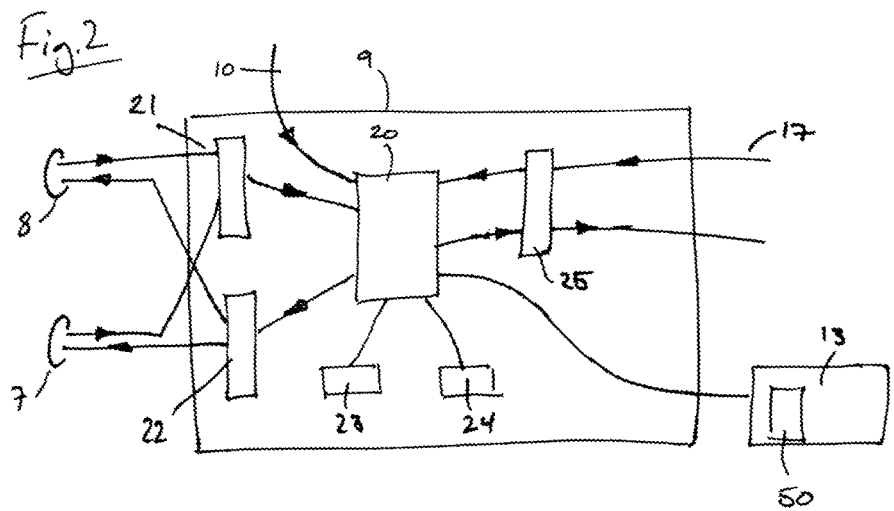
FIG. 2 illustrates a robot controller according to some aspects of the present disclosure.

FIG. 2 shows the control unit 9 in more detail. The control unit 9 comprises a processor 20, an arm input interface 21, an arm output interface 22, a non-volatile memory 23, a temporary data store 24 and a sense inverter 25. The non-volatile memory stores in a non-transient fashion program code that is executable by the processor 20 for causing the control unit 9 to implement the functions described herein. The temporary data store 23 stores temporary information such as the configuration of the robot system. The memories 23, 24 are coupled to the processor 20. The interfaces 21, 22 couple the processor 9 to the lines 7, 8, that carry data to and from the robot arms 1, 2. Data received from each arm, for example from position encoders 30 or force sensors 31 on the joints of the arm or from cameras 32 carried by the arms or as part of an instrument, is passed to the input interface 21 where it is buffered and/or transformed as required in order to be input to the processor 20. Data generated by the processor 20 for controlling the operation of the arms, for example to drive motors 33, 34 which cause motion of the joints of the arms, is processed by the output interface 22 and then transmitted to the arms. The output interface could, for example, increase the voltage and/or current of the output signals as required to drive the arm motors. The arms could be driven by other means, for example hydraulic actuators, in which case the output interface 22 would transform the signals from the processor 20 accordingly. The data communicated to the robot arms along lines 7, 8 could contain information defining values for one or more state variables of the robotic arms 1, 2 and/or the instruments 5, 6. It could for example define the pose of the arm; contain values for one or more joint angles of the arms and/or instrument or a set of motor torques for one or more of the drive motors.

When the robot system is in operation for performing surgery, the bases 3, 4 are placed in suitable locations next to an operating table 40. The required instruments are attached to the robot arms. The control unit is initialised and is configured by means of the operational control unit 13 to cause the robot arms 1, 2 to adopt positions in dependence on the movement of the arm control input devices 14 by the operator. A patient is positioned on the table 40. The operator moves the control arm input devices 14 to provide inputs to the control unit. The control unit interprets those inputs by executing the code stored in memory 23 to generate outputs for controlling the robot arms to undergo the movements commanded by the operator. Meanwhile, a video stream captured by camera 11 or another camera carried by a robot arm is fed to the control unit and from there to the display 15 of the user interface, which displays that video stream to the operator so he can see what the robots are doing.

FIG. 3 shows the control panel 50 of the operational control unit 13. The control panel comprises a number of switches 51-54. These could be physical switches or virtual switches displayed on a touch-sensitive display 55. Each switch is dedicated to performing a particular function. For example, switch 51 provides an input to the control unit 9 which determines whether the control unit will provide video output to the display screens 18 or the headset 19.

There are various ways in which the control arm input devices may control the arms. In one convenient approach the control arm input devices 14 are linkages movable in three dimensions by the operator, and the position of the distal tip (or some other designated part) of each linkage represents the position of a reference part of the mobile elements of the robot. The reference part could, for example, be the distal tip of one of the arms, or alternatively the distal tip of an instrument attached to that arm. The reference part could be the end effector. The processor 9 is configured, by means of the software running on it, so that as a control arm input device is moved by an operator the processor 9 causes the corresponding reference point to move in the same way. Thus, if the distal end of the control arm input device for arm 1 is moved upwards then the reference part on or carried by arm 1 is moved upwards, if the distal part of that control arm input device is moved leftwards then that reference part is moved leftwards, and if that control arm input device is moved away from the operator then that reference part is moved away from a virtual operator position defined with respect to the respective arm. Similarly, translations in the opposite directions, and rotations of the control arm, also cause motions of the respective arm in the same sense. When the operator positions the designated part of the control arm input device this will involve motion of one or more joints along the length of the control arm input device linkage. The processor 9 may position corresponding joints along the length of the respective arm in the same way as the input linkage, or the processor 9 may have authority to position the joints along the arm in any appropriate way that achieves the required position and orientation of the reference point. This latter method may help to avoid collisions between the arms and other equipment in the region of the patient.

The control unit 9 comprises a sense inverter 25. In this example the sense inverter is implemented in hardware, but it could be implemented in software as will be described in more detail below. In this example the sense inverter is located in the communication paths between the processor 20 and both display 15 and the control arm input devices 13, but it could be located elsewhere as will be described in more detail below. The sense inverter is capable of operating in two modes. In a first, normal mode it (a) passes video data unchanged from the processor 20 to the display 15 and (b) passes input data unchanged from the control arm input devices 14 to the processor 20. The configuration of the processor, by virtue of the software that runs on it, is such that in this mode each of the arms 1, 2 is caused to translate or rotate in directions that directly correspond (i.e. are of the same handedness) to the directions of translation or rotation imposed on the respective one of the control arm input devices, as described in the preceding paragraph. In a second, inverting mode the sense inverter (a) receives a video stream from the processor 20 and forms an output video stream which is passed to the display 15 representing the input video stream reflected about a first predetermined plane and (b) receives the control inputs from the control arm input devices and forms an output which is passed to the processor 20 representing those motions reflected about a second predetermined plane (i.e. of the opposite handedness). As a result, when the sense inverter is operating in its inverted mode the operator sees a reflected version of the actual video output from the robot, and the control inputs to the robot are also reflected. The first predetermined plane may be the projection of the centreline of the endoscope camera view. It may be the vertical centreline of the endoscope view, i.e. the first predetermined plane may bifurcate the endoscope view into a left-hand region and a right-hand region. When the first and second planes are appropriately related, as will be described below, this provides the operator with the sensation that the robot is operating normally (i.e. with motions of the same handedness as the control inputs) when in fact the motions being executed by the robot arms are a mirror image of the inputs being provided by the operator. The relationship of the second predetermined plane to the first predetermined plane may be calculated by the sense inverter 25. It may be calculated in hardware of software.

Thus the sense inverter 25, when operating in the inverting mode, may process the video stream captured by the camera 11 (received via the processor 20) to form an output stream that represents the video stream captured by the camera reflected about a first predetermined plane. For example, the sense inverter may buffer a line of video data into memory (e.g. memory 23, temporary data store 24, or some other memory or buffer) and then retrieve that line of data from the buffer in reverse order (i.e. the data is retrieved from the memory in reverse order to the order in which it was input). A line of video data is the pixel data for a single line of pixels of an image of the video stream, i.e. a line of pixels of an image from the sequence of images forming the video sequence. The video stream may be formed from a sequence of images captured by the camera 11. In this case, the sense inverter may, for each image of the stream, buffer a line of video data (i.e. data for a single line of pixels of the image) into memory and then retrieve that line of data in reverse order. This processing step may then be repeated for each pixel line, or row, forming the image to form a single reflected image. This process may then be repeated for each image of the captured video stream whilst the robotic system is operating in inverted mode. This approach is advantageous because it enables the video stream to be reflected by buffering a single line of video data at a time. Thus the memory requirements for reflecting the video feed may be low (the memory need only be sufficient for storing one video line of data).

These normal and inverted modes are illustrated in FIG. 4. FIG. 4a illustrates the normal mode of the sense inverter. FIG. 4a shows at 70 the robot arms 1, 2; at 71 the image of the robot arms 1, 2 that is displayed to the operator; and at 72 the linkages of the control arm input devices. The first plane is indicated at 73 and the second plane is indicated at 74. When the control arm input devices are moved leftwards, as indicated at 75, the arms move leftwards as indicated at 76, and the arms as shown on display 15 also move leftwards. FIG. 4b illustrates the inverted mode of the sense inverter. FIG. 4b shows at 80 the robot arms 1, 2; at 81 the image of the robot arms 1, 2 that is displayed to the operator; and at 82 the linkages of the control arm input devices. The first plane is indicated at 83 and the second plane is indicated at 84. When the control arm input devices are moved leftwards, as indicated at 85, the arms move rightwards as indicated at 86, whilst the arms as shown on display 15 move leftwards. In this example the camera (e.g. camera 11) used to capture the video stream to drive the display has the same spatial position and orientation in both the normal mode and the inverted mode. Thus, in both modes the motion of the arms on the display corresponds in direction/handedness to the direction of the commanded motion, whereas the direction in which the arms actually move is dependent on which mode the sense inverter is operating in.

Rotation is handled in a similar way, so that the actual motion of the arms is either in the same direction/handedness as the motion of the control inputs, when the sense inverter is operating in normal mode; or in a direction reflected about plane 73/83, when the sense inverter is operating in inverted mode.

The first and second axes/planes need not be related in any particular way. However, for intuitive operation of the robot it is preferred that the behaviour of the robot as represented on the display 15 is coordinated with the motion of the control arm input devices. This can be achieved if, as illustrated in FIG. 4, the image on the display 15 is orientated to match the orientation of the control arm input devices and the second plane is then parallel to the first plane as it appears to the operator on the display 15. Preferably the second plane is a vertical plane directed away from the operator position since in this configuration the operator can appreciate the sensation that handedness of the robot's control is inverted by the sense inverter. The first plane may be a vertical plane when the image captured by camera 11 is orientated to match the orientation of the control arm input devices 14. The first plane may be a projection of the centreline of the view captured by the camera 11.

The operating mode of the sense inverter is selected by a dedicated input element 52 of the operational control unit 13.

In addition to reflecting the display output and control inputs, as described above, the sense inverter preferably also swaps the relationship between the control linkages of the operational control unit 13 so that in the normal mode a first one of the control linkages controls a first one of the arms and a second one of the control linkages controls a second one of the arms, whereas in the inverted mode the first one of the control linkages controls the second one of the arms and the second one of the control linkages controls the first one of the arms. This contributes to the sensation that the handedness of the robot's control has been inverted by the sense inverter. This relationship is illustrated in FIG. 5. FIG. 5a illustrates the normal mode of the sense inverter. FIG. 5a shows at 90 the robot arms 1, 2; at 91 the image of the robot arms 1, 2 that is displayed to the operator; and at 92 the linkages of the control arm input devices. The first plane is indicated at 93 and the second plane is indicated at 94. In the normal mode the left-hand control arm input device 95 as viewed by the operator is controlling the left-hand arm 1; and the right-hand control arm input device 96 as viewed by the operator is controlling the right-hand arm 2. When control arm input device 95 is moved upwards as indicated at 97, the associated arm 1 moves upwards as indicated at 98; and when control arm input device 96 is moved downwards as indicated at 99, the associated arm 2 moves downwards as indicated at 100. FIG. 5b illustrates the inverted mode of the sense inverter. FIG. 5b shows at 110 the robot arms 1, 2; at 111 the image of the robot arms 1, 2 that is displayed to the operator; and at 112 the linkages of the control arm input devices. The first plane is indicated at 113 and the second plane is indicated at 114. In the inverted mode the left-hand control arm input device 95 as viewed by the operator is controlling the right-hand arm 2; and the right-hand control arm input device 96 as viewed by the operator is controlling the left-hand arm 1. When control arm input device 95 is moved upwards as indicated at 115, the associated arm 2 moves upwards as indicated at 116; and when control arm input device 96 is moved downwards as indicated at 117, the associated arm 1 moves downwards as indicated at 118.

Thus, in both modes the control device operates so that the displayed image of the arms depicts the arms moving with the same handedness as the control inputs, whereas in the second mode the arms are in fact moving with the opposite handedness to the control inputs. The normal or non-reflected image shown by the display in the first mode depicts the motions of the arms unreflected from their actual state, whereas in the second mode the motions of the arms are depicted reflected from their actual state.

In normal operation the input element 52 is set so that the sense inverter operates in its normal mode. The operator is controlling a first one of the robot arms (arm A) with his right hand and the other of the robot arms (arm B) with his left hand. Suppose the operator is right-handed. When the operator reaches a point in the procedure where he needs to operate arm B with particular dexterity he can operate the input element 52 to switch the sense inverter into inverting mode. Then: (a) he will see on the display 15 a mirror image of the actual operating site; (b) the robot arms will move in senses that are mirrors of the senses in which their respective controlling means are operated; and (c) the controlling means operated by the operator's right hand, which was previously controlling arm A is now controlling arm B. Now the operator can operate the arms in an entirely intuitive way even though the image being displayed to the operator and the relationship between the operator's movements and the movements of the arms are actually mirrored.

When the sense inverter is implemented in hardware, as illustrated in FIG. 2, it may operate for video by receiving a video frame, transforming it by applying the appropriate reflection and then transmitting it on; and for control inputs by applying the appropriate changes to the incoming signals so that they are as if the control inputs had been reflected. The sense inverter could alternatively be located between the arm input/output buffers 21, 22 and the processor 20, inverting the signals to and from the arms as required. The sense inverter could alternatively be implemented by software embodied by code stored in memory 23 and running on processor 20 to make the necessary adaptations to the way in which the inputs from the input device 14 are interpreted and to transform the video stream.

Figure 6:
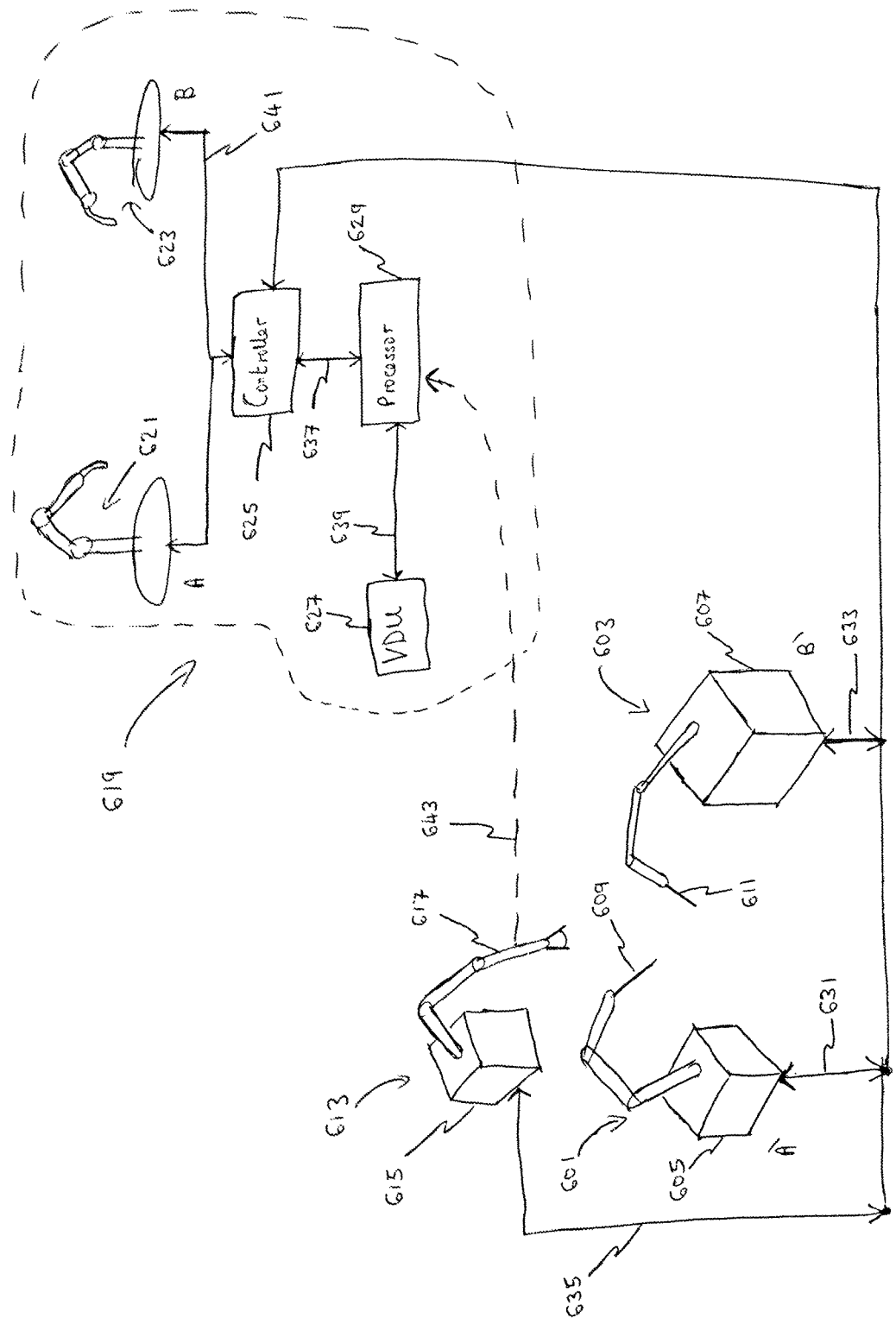
FIG. 6 shows an alternative example of a surgical robotic system according to some aspects of the present disclosure.

An alternative arrangement of the surgical robotic system is shown in FIG. 6. The system comprises two robotic arms 601 and 603 (also labelled as A' and B' respectively). Each arm comprises a series of rigid links joined by articulated joints, as described above with respect to FIG. 1. The proximal end of each arm is mounted onto a base 605 and 607. The distal end of each arm 601 and 603 terminates in a surgical instrument 609 and 611. The distal ends of the instruments may terminate in an end effector.

The system further comprises a third robotic arm 613. Arm 613 is attached to base 615. The arm 613 carries an endoscope 617. The endoscope may be mounted onto the arm. The endoscope is positioned to view the surgical site and the distal ends of the robotic arms 601 and 603.

The robotic system comprises a surgeon's console 619, depicted by the dashed markings. The surgeon's console comprises two input controllers 621 and 623 (also labelled as 'A' and 'B' respectively). The input controllers operate in a similar manner to the input devices 14 described above. That is, the input controllers 621 and 623 provide a user interface whereby an operator of the system can indicate, or input, desired motions of the robotic arms 601 and 603. In other words, the user can manipulate the input controllers to effect desired motion of the robotic arms 601 and 603. One or both of the input controllers 621 and 623 may comprise an additional user input interface to receive inputs from a user to control the motion of the robotic arm 613 and thus the endoscope 617. As described above with reference to FIG. 1, this input interface may be in the form of a thumb joystick attached to one of the input controllers.

The system further comprises a controller 625, a video display unit (VDU) 627 and a display processor 629. The processor 629 controls the format of the video feed fed to the VDU and so may be referred to as display unit. The controller 625 may be referred to as a motion controller. The controller 625 is coupled to each of the robotic arms 601, 603 and 613 via a series of data buses 631, 633 and 635. The controller 625 is further coupled to the processor 629 via data bus 637. The display processor 629 is coupled to the VDU via data bus 639 and to the input controllers by data bus 641. The endoscope 617 communicates captured video data to the display processor 629 as indicated by the arrow 643. The endoscope may be coupled to the display processor 629 by a data cable (not shown) for communicating the video data.

The operator can manipulate the input controllers 621 and 623 to effect motion of the robotic arms 601, 603 and 613. The input controllers may comprise sensors (not shown) for sensing the configuration of each controller. Information on the configuration of the input controllers is passed from the controllers to the motion controller 625 via data bus 641.

The controller 625 receives data from the input controllers indicating the movement and/or configuration of the input controllers and processes that received data to generate control data that is communicated to the robotic arms via data buses 631, 633 and 635 as appropriate. As mentioned above, that control data may include values for a set of one more state variables of the robotic arms, such as joint angles (to define a pose, or orientation, of the robotic arms), or drive motor torques to effect movement of one or more joints of the robotic arms, etc.). Thus the controller 625 operates to map the configuration and/or position of the input controllers to the configuration and/or position of the robotic arms. The controller 625 may be configured to map a reference point of the input controllers (e.g. the handle of the controller) to a respective reference point on the robotic arm. The reference point on the robotic arm may be the end effector. For arm 613 the reference point may be the endoscope, e.g. the camera of the endoscope. This may provide the user of the system with particularly intuitive control over the position of the end effectors and endoscope. Processor 20 may be an example of the motion controller 625.

In this example video data captured by the endoscope is communicated to the processor unit 629 as indicated by the arrow 643 (e.g. by a data cable connected to the endoscope and display processor 629, or by a wireless network). The processor unit 629 passes that data (either processed or unprocessed) to the video display unit 627, where it is displayed to the user. Thus the VDU is operable to display video data derived from video data captured by the endoscope. The VDU may take different forms; for example it could be in the form of a display screen, or alternatively in the form of a wearable headset.

Like the robotic system shown in FIG. 1, the robotic system shown in FIG. 6 can operate in a 'normal' operational mode and an 'inverted' operational mode. In a normal mode the display processor 629 passes video data from the endoscope unchanged to the VDU so that the VDU displays the image captured by the endoscope. Further, in normal mode the controller 625 passes input data unchanged from the input controllers 621, 623 to the robotic arms 601, 603 and 613. The controller 625 is arranged to process the inputs from the input controllers so that, in this mode, the arms 601, 603 and 613 translate and/or rotate in directions that directly map to the directions of translation and/or rotation of the input controllers. In other words, manipulation of the controllers 621 and 623 may correspond directly to the resultant manipulations of the robotic arms (i.e. be of the same handedness).

In inverted mode, data received by the controller 625 may be processed in two ways. Firstly, the controller 625 may instruct the display processor 629 to enter 'reflecting', or 'mirroring' mode so that the video data from the endoscope received by the display processor 629 is processed to be reflected about a first predetermined plane. The display processor 629 then passes this processed (i.e. reflected) data to the VDU 627 so that the VDU displays the reflected video data (i.e. the VDU displays the video data captured by the endoscope but reflected about the first plane). As in the examples above, the first plane may be a projection of the vertical centreline of the endoscope camera view. Secondly, input data received from the input controls 621 and 623 representing a movement of the controls is processed by the controller 625 to represent that movement reflected about a second predetermined plane. The controller 625 may then output control information to the robotic arms 601, 603 and 613 containing values for a set of one or more state variables corresponding to the reflected movement of the input handles. In other words, the controller 625: i) processes input data representing movement of the input controllers 621 and 623 to represent those movements reflected about a second plane; and ii) generates control information to cause the robotic arms to move in a direction that directly corresponds to the reflected movements.

The display processor 629 may comprise a buffer, or memory (not shown). To reflect the video feed from the endoscope, the processor 629 may buffer a line of the video data into memory and then read the data from the memory in reverse order to the order in which the data was input. Here, a line of video data is data for a line of pixels (e.g. pixel values) of an image forming part of the captured image sequence that forms the video stream. This is convenient because it means that the buffer need only have capacity to store a single line of video data, meaning the video feed can be reflected without requiring a buffer large enough to store an entire image. Of course, other video-reflecting techniques could be used in the alternative.

The operational mode of the robotic system and the transition of the system from one operating mode to the other may be independent of the position, attitude, or orientation of the camera 617.

The first and second planes described in this example may have the same relationship to each other as the planes described above with reference to FIGS. 1 to 5.

Video data from the endoscope may be communicated to the display processor 629 using a wireless communication network rather than by a data cable.

The controller 625 may be further configured to switch the association between the input controllers A, B and the robotic arms A', B' in the inverted mode. In normal mode, input controller A is associated with robotic arm A' so that movement of input controller A causes movement of arm A'. Similarly, input controller B is associated with robotic arm B'. In inverted mode, the controller 625 may swap these associations so that input controller B is associated with robotic arm A' and input controller A is associated with robotic arm B'. This may enhance the intuitiveness of the system to the user when in reflecting mode.

The processor 629 operates to either pass video data from the camera 617 unprocessed to the VDU for display or to pass processed video data (i.e. video data received from the camera and reflected about the second plane) to the VDU for display. The display processor 629 passes either the processed or unprocessed data under the control of the controller 625. That is, the controller 625 issues an instruction to the processor 629 to cause the processor to process the video data to reflect it, or to cause the display processor to pass the video data to the VDU unprocessed. The controller 625 may itself be instructed to operate in normal or inverted mode by a hardware switch (e.g. input element 52).

The controller 625 may be implemented in hardware (e.g. as a dedicated hardware unit) or in software. If implemented in software, it may be stored in non-transitory form as program code in a non-volatile memory of the surgeon's console (not shown) and be executed by a processing unit to execute the functions described herein. The display processor 629 may also be implemented in hardware (e.g. as a dedicated hardware unit) or software that may be stored in non-transitory form as program code in a non-volatile memory for execution by a processor to execute the functions described herein.

In the robotic systems described herein (e.g. those with reference to FIGS. 1 to 6), the system is arranged to perform three different processes when switching from normal mode to reflected mode (or vice versa). These are: i) the video feed received from the camera/endoscope is processed to be reflected about a first predetermined plane; ii) data received from input controllers (e.g. controllers 14, 621, 623) representing a movement of the input controllers are processed to represent those controller movements reflected about a second predetermined plane; and iii) the association between the input controllers and the robotic arms is swapped. Each of these processes has been described in detail herein.

Of course, each of the systems described herein may be arranged to perform any combination of these processes when swapping modes of operation. For example, the system may reflect the video feed and process the data from the input controllers to represent the controller movements reflected about a plane (i.e. it may perform processes i) and ii)). It may alternatively reflect the video feed and swap the association between the input controllers and the robotic arms (i.e. it may perform processes i) and iii)). Alternatively still it may process the data from the input controllers representing a movement of the input controllers to represent those movements reflected about the second predetermined plane and swap the association between the input controllers and the robotic arms (i.e. it may perform processes ii) and iii). It may perform any of the processes in isolation (i.e. perform process i); process ii) or process iii)).

In the examples herein, the processing units (e.g. control unit 9; controller 625; display processor 629) may form part of the general processing unit of the robotic system. Although shown as separate components to the robot arms and base in FIGS. 2 and 6, this is an example only. Any of the units/controllers may be positioned within a general processing unit of the robotic system and housed or integrated within the robotic system, e.g. within one of the robotic arms, or within the base of the robot.

In the examples described above, the control signals from the control arm input devices 14 are communicated to the control unit 9 via lines 17. The lines may be physical data lines (e.g. data cables, data bus etc.), or they may be illustrative of a logical connection between the input devices 14 and the control unit. For example, control information from the control arm input devices may be communicated wirelessly from the sensors of the devices to the control unit over a communication network. This network may be a local area network. Similarly, video data captured by the endoscope may be communicated wirelessly from the endoscope to the control unit. The control unit may then perform the necessary processing of the movement data of the control arm input devices and the video data (as described above) and communicate the data for controlling the robot arms to the robot arms over a wireless communication network. In other words, the control unit 9 may be located separately from the input devices 14 and the robotic arms. Lines 7, 8, 10 and 17 may each represent logical connections between the control unit and the input devices and robotic arms 1, 2. Communicating data to and/or from the control arm input devices and to and/or from robotic arms over a wireless communication network may conveniently enable a surgeon to perform a procedure remotely. That is, the surgeon's control station may be geographically remote from the robotic arms 1, 2. This is similarly the case for the robotic system shown in FIG. 6. Here, data is communicated between various components of the robotic system via bidirectional data buses. In other examples, each of the data buses (e.g. buses 631, 633 and 635) may be replaced by a wireless communication connection to enable data to be communicated over a wireless network.

In the examples above the robotic system can be switched from the normal mode to inverting mode, and vice versa, by the input element 52, which may be a dedicated switch or button. In other examples the operational mode may be switched by a software mode, e.g. executed on processor 20 of the control unit 9. In this case there may be no need for input element 52. The software mode may be activated to switch the operational mode of the robotic system. The mode may be activated in response to a number of different conditions. It may for example be voice-activated. The switching of the operational mode may be independent of the position, orientation and attitude of the camera 11.

In the examples given above the input devices 14 and 621, 623 are mechanical, but they could be implemented by remotely sensing the motion of the operator's body.

The robotic system could comprise two robot arms, as illustrated in FIG. 1, or just one robot arm, or more than two (e.g. as shown in FIG. 6). The robot arms could be articulated in any suitable manner.

The display could show one or both of the arms (e.g. if the video is captured by a camera 11, 617 that has a view of the arms) or could be moved by one of the arms (as in the case of camera 32) in which case it need not show that or the other arm.

The processor 20 could be implemented by one or more individual processor devices or cores.

The control unit 9 could be in a single housing or distributed between multiple housings.

The controller 625 could be implemented by one or more individual processor devices or cores. Similarly for the display processor 629. The display processor 629 and controller 625 may be integrated as a single processor unit or core.

The location at which the operator works could be nearby the robot arms or remote.

The robots could be used for non-surgical purposes.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic system comprising:
   a robot arm;
   a camera for capturing a video stream representing motion of the robot arm;
   an input mechanism for detecting the motion of a user;
   a display device; and
   a controller for driving the robot arm to operate in response to motion of the user as detected by the input mechanism and for driving the display device to display a video stream captured by the camera;

the controller being capable of operating in:
- a first mode in which the controller drives the display device to display the captured video stream in a first format and in which the controller drives the robot arm such that motion by the user in a first direction as detected by the input mechanism causes the robot arm to move a reference part in a second direction; and
- a second mode in which the controller drives the display device to display the captured video stream in a second format that is reflected with respect to the first format and in which the controller drives the robot arm such that motion by the user in the first direction as detected by the input mechanism causes the robot arm to move the reference part in a direction opposite to the second direction.

2. A robotic system as claimed in claim 1, the system comprising a second robot arm, the input mechanism being capable of independently detecting motion of two hands of the user, and the controller being configured so as to:
- in the first mode drive the motion of a first one of the robot arms in dependence on a motion sensed in respect of a first hand of the user, and the motion of a second one of the robot arms in dependence on a motion sensed in respect of a second hand of the user; and
- in the second mode drive the motion of the second one of the robot arms in dependence on a motion sensed in respect of the first hand of the user, and the motion of the first one of the robot arms in dependence on a motion sensed in respect of the second hand of the user.

3. A robotic system as claimed in claim 1, wherein the input mechanism comprises one or more mechanical linkages, each linkage being movable by a respective hand of the user to detect motion of the user.

4. A robotic system as claimed in claim 1, wherein the input mechanism comprises one or more detectors configured for remotely sensing the motion of the user.

5. A robotic system as claimed in claim 1, wherein the second format is a format in which the captured video stream is reflected about an axis that is vertical with respect to the display device.

6. A robotic system as claimed in claim 1, wherein the second format is a format in which the captured video stream is reflected about an axis that is vertical with respect to the user.

7. A robotic system as claimed in claim 1, wherein the first direction is horizontal.

8. A robotic system as claimed in claim 1, wherein the controller is configured such that, in both the first and second modes, the controller drives the robot arm such that motion of the user in a third direction orthogonal to the first direction as detected by the input mechanism causes motion of the reference part in a fourth direction orthogonal to the second direction.

9. A robotic system as claimed in claim 1, comprising a dedicated input device for selecting whether the controller operates in the first mode or the second mode.

10. A robotic system as claimed in claim 1, wherein the reference part is the distal end of the robot arm.

11. A robotic system as claimed in claim 1, wherein the reference part is the distal tip of an instrument mounted on the arm.

12. A robotic system as claimed in claim 1, wherein the camera is carried by a further robot arm.

13. A robotic system as claimed in claim 1, the system being a surgical robotic system.

14. A robotic system comprising:
- a first robot arm;
- a second robot arm;
- a camera for capturing a video stream representing motion of the first and second robot arms;
- a display device;
- an input mechanism for detecting the motion of a user, the input mechanism being capable of independently detecting motion of two hands of the user; and
- a controller for driving the robot arm to operate in response to motion of the user as detected by the input mechanism, the controller being configured so as to:
  - in a first mode (i) drive the motion of a first one of the robot arms in dependence on a motion sensed in respect of a first hand of the user, (ii) drive the motion of a second one of the robot arms in dependence on a motion sensed in respect of a second hand of the user, and (iii) drive the display device to display the captured video stream in a first format; and
  - in a second mode (i) drive the motion of the second one of the robot arms in dependence on a motion sensed in respect of the first hand of the user, (ii) drive the motion of the first one of the robot arms in dependence on a motion sensed in respect of the second hand of the user, and (iii) drive the display device to display the captured video stream in a second format that is reflected with respect to the first format.

15. A robotic system as claimed in claim 14, wherein the second format is a format in which the captured video stream is reflected about an axis that is vertical with respect to the display device.

16. A robotic system as claimed in claim 14, wherein the second format is a format in which the captured video stream is reflected about an axis that is vertical with respect to the user.

17. A robotic system as claimed in claim 14, comprising a dedicated input device for selecting whether the controller operates in the first mode or the second mode.

18. A robotic system as claimed in claim 14, wherein the camera is carried by a third robot arm.

19. A robotic system as claimed in claim 14, the system being a surgical robotic system.

* * * * *